United States Patent
Adler et al.

(10) Patent No.: US 7,855,727 B2
(45) Date of Patent: Dec. 21, 2010

(54) ENDOSCOPY DEVICE SUPPORTING MULTIPLE INPUT DEVICES

(75) Inventors: Doron Adler, Nesher (IL); Shai Finkman, Haifa (IL); Arie Blumzvig, Natumia (IL)

(73) Assignee: Gyrus ACMI, Inc., Southborough, MA (US)

( * ) Notice: Subject to any disclaimer, the term of this patent is extended or adjusted under 35 U.S.C. 154(b) by 1270 days.

(21) Appl. No.: 10/942,210

(22) Filed: Sep. 15, 2004

(65) Prior Publication Data

US 2006/0055793 A1   Mar. 16, 2006

(51) Int. Cl.
- H04N 9/47 (2006.01)
- H04N 7/18 (2006.01)
- H04N 5/232 (2006.01)
- A62B 1/04 (2006.01)
- A61B 1/04 (2006.01)

(52) U.S. Cl. .............................. 348/65; 348/64; 348/72; 348/211.99; 348/211.14

(58) Field of Classification Search .................. 348/64, 348/65, 72, 211.99, 211.14
See application file for complete search history.

(56) References Cited

U.S. PATENT DOCUMENTS

| | | | |
|---|---|---|---|
| 4,298,260 A | 11/1981 | Takayama | 396/17 |
| 4,403,605 A | 9/1983 | Tanikawa | 600/109 |
| 4,561,427 A | 12/1985 | Takada | 600/114 |
| 4,827,908 A | 5/1989 | Matsuo | 600/109 |
| 4,860,094 A | 8/1989 | Hibino et al. | 600/109 |
| 4,926,258 A | 5/1990 | Sasaki et al. | 348/72 |
| 5,040,068 A | 8/1991 | Parulski et al. | |
| 5,124,797 A | 6/1992 | Williams et al. | 348/340 |
| 5,153,721 A * | 10/1992 | Eino et al. | 382/152 |
| 5,162,913 A | 11/1992 | Chatenever et al. | 348/230.1 |
| 5,408,265 A | 4/1995 | Sasaki | 348/70 |
| 5,419,312 A | 5/1995 | Arenberg et al. | 600/108 |
| 5,475,420 A * | 12/1995 | Buchin | 348/72 |
| 5,585,840 A | 12/1996 | Watanabe et al. | 348/65 |
| 5,598,218 A | 1/1997 | Inoue | 348/443 |

(Continued)

FOREIGN PATENT DOCUMENTS

JP   HEI4-4504945   8/1992

(Continued)

OTHER PUBLICATIONS

Office Action from the Patent Office of Japan dated Jan. 5, 2010 for corresponding Japanese patent application No. 2007-531484, (with English summary) 4 pages.

(Continued)

*Primary Examiner*—Marsha D Banks Harold
*Assistant Examiner*—Chikaodili E Anyikire
(74) *Attorney, Agent, or Firm*—Ganz Law, P.C.

(57) ABSTRACT

The present invention provides a remote-head imaging system with a camera control unit capable of supporting multiple input devices. The camera control unit detects an input device to which it is connected and changes the camera control unit's internal functionality accordingly. Such changes includes altering clock timing, changing video output parameters, and changing image processing software. In addition, a user is able to select different sets of software program instructions and hardware configuration information based on the head that is attached. The remote-head imaging system utilizes field-programmable circuitry, such as field-programmable gate arrays (FPGA), in order to facilitate the change in configuration.

13 Claims, 10 Drawing Sheets

U.S. PATENT DOCUMENTS

| | | | | |
|---|---|---|---|---|
| 5,682,199 | A | | 10/1997 | Lankford ................... 348/72 |
| 5,696,553 | A | * | 12/1997 | D'Alfonso et al. ..... 348/211.14 |
| 5,732,704 | A | | 3/1998 | Thurston et al. ........... 600/431 |
| 5,740,801 | A | | 4/1998 | Branson .................... 600/407 |
| 5,857,463 | A | | 1/1999 | Thurston et al. ........... 600/436 |
| 5,868,666 | A | * | 2/1999 | Okada et al. ............... 600/118 |
| 5,896,166 | A | | 4/1999 | D'Alfonso et al. ........... 348/72 |
| 6,002,425 | A | | 12/1999 | Yamanaka et al. ........... 348/68 |
| 6,046,769 | A | * | 4/2000 | Ikeda et al. ............... 348/222.1 |
| 6,154,248 | A | | 11/2000 | Ozawa et al. ................. 348/65 |
| 6,184,922 | B1 | | 2/2001 | Saito et al. .................... 348/65 |
| 6,201,570 | B1 | * | 3/2001 | Murata et al. ............ 348/211.5 |
| 6,224,542 | B1 | | 5/2001 | Chang et al. ................. 600/109 |
| 6,295,082 | B1 | | 9/2001 | Dowdy et al. ................. 348/72 |
| 6,313,868 | B1 | | 11/2001 | D'Alfonso et al. ........... 348/72 |
| 6,414,714 | B1 | | 7/2002 | Kurashige et al. |
| 6,462,770 | B1 | | 10/2002 | Cline et al. ................... 348/65 |
| 6,503,195 | B1 | | 1/2003 | Keller et al. ................. 600/160 |
| 6,511,422 | B1 | | 1/2003 | Chatenever ................. 600/180 |
| 6,538,687 | B1 | | 3/2003 | Saito et al. .................... 348/65 |
| 6,540,671 | B1 | | 4/2003 | Abe et al. ................... 600/180 |
| 6,591,130 | B2 | | 7/2003 | Shahidi ....................... 600/424 |
| 6,593,962 | B1 | * | 7/2003 | Downer et al. ......... 348/211.99 |
| 6,625,299 | B1 | | 9/2003 | Meisner et al. ............. 382/103 |
| 6,638,212 | B1 | | 10/2003 | Oshima ....................... 600/109 |
| 6,652,451 | B2 | | 11/2003 | Murata et al. ............... 600/118 |
| 6,669,628 | B2 | | 12/2003 | Abe ............................ 600/118 |
| 6,677,984 | B2 | | 1/2004 | Kobayashi et al. ............ 348/65 |
| 6,692,430 | B2 | | 2/2004 | Adler |
| 6,707,490 | B1 | * | 3/2004 | Kido et al. ............. 348/211.14 |
| 6,715,068 | B1 | | 3/2004 | Abe ............................... 713/1 |
| 6,738,091 | B1 | * | 5/2004 | Eouzan et al. ......... 348/211.14 |
| 7,212,227 | B2 | * | 5/2007 | Amling et al. ................ 348/72 |
| 7,300,397 | B2 | | 11/2007 | Adler et al. |
| 7,453,490 | B2 | | 11/2008 | Gunday |
| 7,471,310 | B2 | * | 12/2008 | Amling et al. ................ 348/72 |
| 2001/0035902 | A1 | | 11/2001 | Iddan et al. |
| 2001/0051762 | A1 | | 12/2001 | Murata et al. |
| 2002/0191082 | A1 | * | 12/2002 | Fujino et al. ........... 348/211.14 |
| 2002/0196334 | A1 | | 12/2002 | Saito et al. |
| 2003/0025789 | A1 | | 2/2003 | Saito et al. |
| 2003/0030722 | A1 | | 2/2003 | Ozawa et al. |
| 2003/0123856 | A1 | | 7/2003 | Chatenever et al. |
| 2003/0142753 | A1 | | 7/2003 | Gunday |
| 2003/0174205 | A1 | * | 9/2003 | Amling et al. ................. 348/65 |
| 2003/0184645 | A1 | | 10/2003 | Biegelsen et al. |
| 2003/0197790 | A1 | * | 10/2003 | Bae ....................... 348/211.99 |
| 2003/0236446 | A1 | | 12/2003 | Eino |
| 2004/0019255 | A1 | | 1/2004 | Sakiyama |
| 2004/0028390 | A9 | * | 2/2004 | Chatenever et al. ......... 386/107 |
| 2005/0182299 | A1 | | 8/2005 | D'Amelio et al. |
| 2007/0276182 | A1 | | 11/2007 | Adler et al. |

FOREIGN PATENT DOCUMENTS

| | | |
|---|---|---|
| JP | HEI 7-240866 | 9/1995 |
| JP | HEI 10-19122 | 1/1998 |
| WO | WO9110320 A1 | 7/1991 |
| WO | WO96/11548 | 4/1996 |

OTHER PUBLICATIONS

PCT International Search Report and Written Opinion dated Apr. 20, 2006 for International Application No. PCT/US05/33101, filed Sep. 14, 2005, 9 pages.

"Olympus News Release: VISERA Video System Launched Globally" (Jun. 28, 2002) viewed at http://www.olympus.co.jp/en/news/2002a/nr020628viserae.cfm?ote=0&nr=1 on Sep. 13, 2004.

Advertizing Literature, "Olympus' Visera Endoeye vs. The Competition" (date unknown).

Olympus Product Bulletin No. 399, "LTF-V3 VISERA Laparo-Thoraco Videoscope" (Oct. 3, 2002).

Advertizing Literature, "Visera Camera Box" (date unknown).

Japanese Office Action dated Jul. 27, 2010, for related Japan Patent Application No. 2007-531484; an informal English summary of the Office Action provided by the Japanese agent is included; 3 pages total.

* cited by examiner

ENDOSCOPY DEVICE SUPPORTING MULTIPLE INPUT DEVICES

BACKGROUND AND SUMMARY

1. Field of the Invention

The present invention generally relates to remote-head imaging, and more particularly, to an endoscopy device with a multi-purpose camera control unit that supports multiple input devices.

2. Description of the Related Art

Remote-head imaging devices, and more particularly, endoscopes and video-endoscopes, are used in medical and industrial applications to view inside of cavities, bodily canals, hollow organs, and other remote locations. Typically, video-endoscopes consist of an input device, such as a distal-end (the end closest to the patient) camera on a rigid or flexible scope, that is attached to a camera control unit. The camera control unit typically supplies power to the camera, controls operation of the camera, receives raw video and non-video data from the camera, and outputs processed video data to a video display.

Conventional camera control units for video-endoscopes and remote-head imaging systems are limited in use, however, as they only support one type of input device. For example, a conventional camera control unit for a flexible scope with a distal-end camera would be unable to control a stereoscopic imaging head. In conventional systems, if a different input device is necessary for a certain application, it is also necessary to use a different camera control unit adapted for use with the specific input device.

SUMMARY OF THE INVENTION

The present invention addresses these shortcomings by providing a remote-head imaging system with a camera control unit that reconfigures itself and/or its internal functionality so as to support multiple different input devices.

In accordance with one aspect of the present invention, a camera control unit is provided for controlling operation of a sensor head and for processing camera data received from the sensor head. The camera control unit includes an electrical interface detachably connectable to sensor heads of multiple different sensor types, and a reconfigurable controller for timing and control of the electrical interface. The camera control unit also includes a system controller which obtains identification information from the sensor head and reconfigures the reconfigurable controller for timing and control of the electrical interface based on the identification information obtained from the sensor head.

In preferred aspects of the invention, the reconfigurable controller is a field-programmable gate array ("FPGA").

In accordance with another aspect of the present invention, the camera control unit includes a reconfigurable controller for timing and control of the sensor head, for receiving camera data from the sensor head, and for directing the camera data along a data path. A digital signal processor performs an image processing operation on camera data on the data path. The reconfigurable controller may be constructed from a hardware device with programmable functionality, such as a FPGA. The camera control unit also includes persistent re-writeable memory for storing program instructions or code executable by the digital signal processor to perform the image processing operation, and configuration information for configuring the reconfigurable controller to perform the timing and control, and otherwise to change the functionality of the camera control unit. The camera control unit further includes a system controller for loading the program instructions into the digital signal processor and for configuring the reconfigurable controller in accordance with the configuration information. By utilizing a persistent re-writeable memory for storing program instructions for the digital signal processor and configuration information for the reconfigurable controller, the present invention allows for updating functionality of the camera control unit in the field.

According to another aspect of the present invention, the camera control unit includes a reconfigurable controller for timing and control of the sensor head, for receiving camera data from the sensor head, and for performing a pixel preprocessing operation on the received camera data. The camera control unit further includes a digital signal processor for performing an image processing operation on the received camera data. In addition, the camera control unit includes a persistent re-writeable memory for storing multiple sets of program instructions executable by the digital signal processor to perform an image processing operation, and for storing multiple sets of configuration information for configuring the reconfigurable controller to perform the timing and control and pixel preprocessing operation. An input device allows for the selection of a set of program instructions to be used by the digital signal processor and selection of the configuration information for the reconfigurable controller. The camera control unit also includes a system controller for loading the selected set of program instructions into the digital signal processor and for reconfiguring the reconfigurable controller in accordance with the selected configuration information. In this way, a user can select specific processing operations and hardware configurations to be performed by the camera control unit.

According to yet another aspect of the present invention, the camera control unit includes a reconfigurable display formatter for formatting a display of the processed camera data and for generating an output timing signal, a video format selection unit for selecting one of the plurality of video formats, and a system controller for reconfiguring the reconfigurable display formatter for formatting and generating the output timing signal in response to the selection of a video format within the video format selection unit.

According to another aspect of the present invention, the camera control unit includes a hardware clock for generating a clock signal, a digital signal processor (DSP) for receiving the hardware clock signal and for generating a DSP clock signal from the hardware clock signal, and a reconfigurable controller that receives sensor data based on a first clock signal and that outputs processed video data based on a second clock signal. The reconfigurable controller includes a reconfigurable logic array that receives the DSP clock signal and generates the first and second clock signals. In addition, a system controller is provided which reconfigures the logic array to generate selectably different first and second clock signals. In this way, input and output clock signals can be independently generated and adjusted from the same hardware clock signal.

According to still another aspect of the present invention, the camera control unit includes a reconfigurable controller, a digital signal processor, including an input memory and an output memory, for image-processing of camera data in the input memory and outputting the processed camera data to the output memory, and a video encoder. The reconfigurable controller receives camera data from the sensor head and routes the camera data to the input memory of the digital signal processor. In addition, the reconfigurable controller accesses the processed camera data from the output memory of the digital signal processor and routes the processed camera data to the video encoder. In this way, the digital signal processor can be devoted to image-processing of the camera data, since it is the reconfigurable controller that deposits data for processing in the input memory and retrieves processed data from the output memory.

In another aspect of the invention, a camera control unit is provided for controlling the operation of a remote-head input device, for receiving and processing digital camera data from the remote-head input device, and for outputting the processed data to a monitor. Typically, the remote-head input device used with the camera control unit of the present invention is an electronic video-endoscope, or a snap-on type camera head configured to be detachably mounted to the eyepiece of a conventional endoscope.

One feature of the camera control unit is that the camera control unit adapts to multiple different types of camera heads. For example, the camera heads may contain sensors that vary in size, speed, or resolution. To adapt to these different camera heads, the camera control unit reconfigures its internal functionality by loading specific sets of software (program instructions) and firmware (as defined by configuration information) in response to the detection and recognition of an attached camera head.

Another feature of the invention is that the camera control unit reconfigures control circuitry using specific configuration information so that video can be output in a plurality of different formats. In this way, for example, both NTSC and PAL television standards can be supported.

Other features of the present invention include hardware acceleration, clock adjustability, user selectable configuration, and field programmable software and firmware.

This summary has been provided so that the nature of the invention may be understood quickly. A more complete understanding of the invention can be obtained by reference to the following detailed description, appended claims, and accompanying drawings.

DETAILED DESCRIPTION

Figure 1:
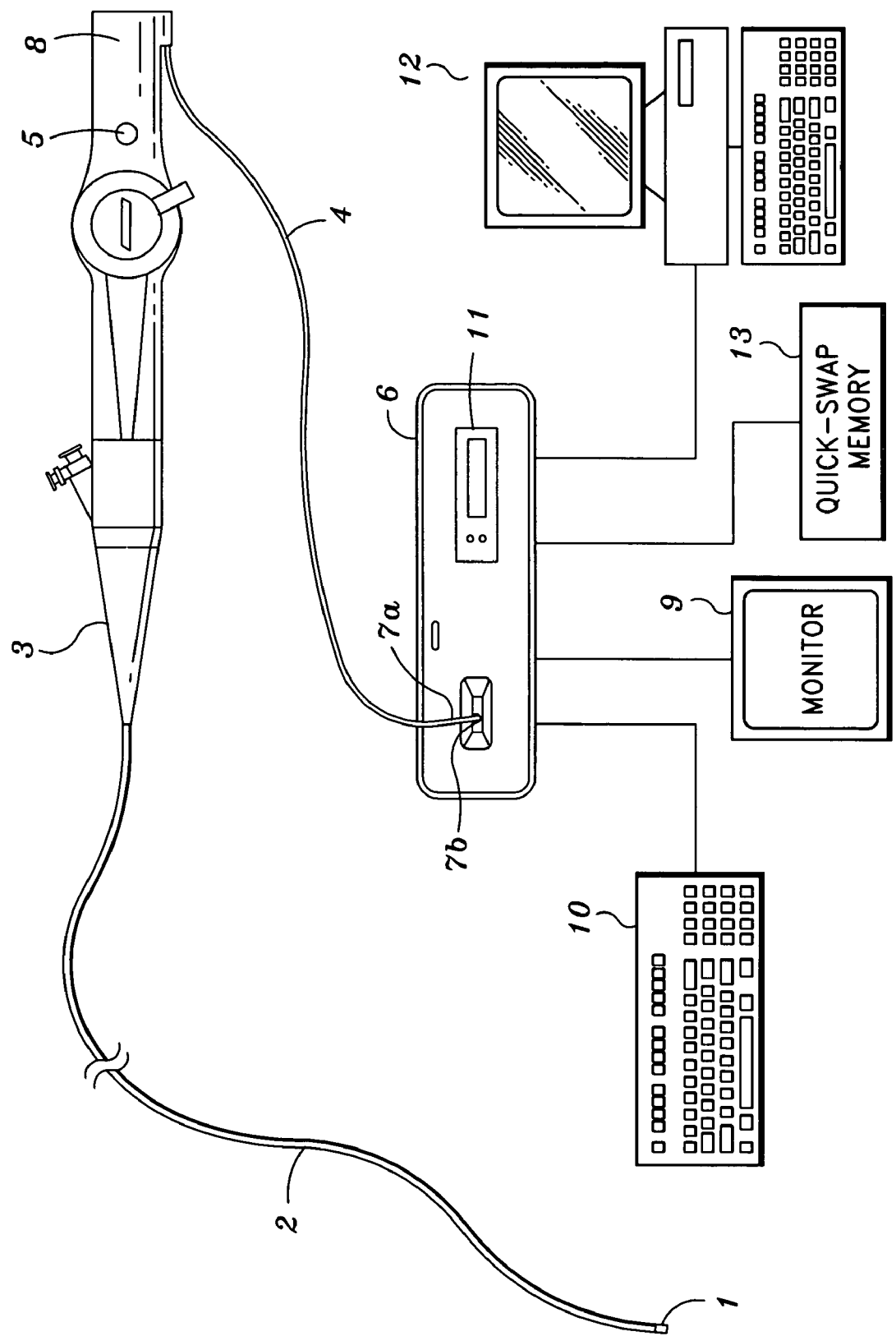
FIG. 1 is an overview diagram of a video endoscope system in accordance with an exemplary embodiment of the present invention.

Referring now to the drawings, FIG. 1 depicts one possible configuration of the present invention. Camera control unit 6 is connected to flexible video endoscope 8 as well as monitor 9, keyboard 10, PC 12 and quick-swap memory device 13. In general, image data is captured by an image sensor located in distal tip 1 of endoscope 8 and is supplied to camera control unit 6 through umbilicus 4. Camera control unit 6 processes the image data, and formats the processed data to be output to monitor 9. User inputs to camera control unit 6 are achieved through keyboard 10, user interface 11, or PC 12. User interface 11 could include, but is not limited to, status LED's, switches, tactile buttons and LCD screens.

Flexible video endoscope 8 is connected to camera control unit 6 by attaching electrical connector 7A of umbilicus 4 to complementary connector 7B of camera control unit 6, which might be a card edge receptacle. Flexible video endoscope 8 includes distal tip 1, endoscope shaft assembly 2, endoscope body assembly 3, and sealed endoscope switches 5.

Distal tip 1 includes a camera head and a mechanical objective head which encloses and seals the camera head. Located in the camera head is an optical system, which includes an image sensor, sensor support electronics, an illumination end point, and forcep tubing. Preferably, the image sensor is a CMOS sensor, however, other sensors that capture image data and generate a digital output may also be utilized. The illumination end point may be implemented as an LED or the end of a fiber optic bundle.

Endoscope shaft assembly 2 houses an electrical wiring portion of the camera head, forcep tubing, and deflection pull wires. In addition, the endoscope shaft assembly may also contain a fiber optic illumination bundle, if used.

Endoscope body assembly 3 contains mechanical mechanisms used to activate the deflection system as well as support electronics for the camera head. Typically, the support electronics in endoscope body assembly 3 will include a permanent storage device, such as an EPROM, that stores camera parameters that define the type of camera head.

Sealed endoscope switches 5, keyboard 10, user interface 11 allow the user to control certain electrical and/or software features of the camera head. In addition, the switches on the endoscope may be used to select processing to be performed by the camera control unit. PC 12 and quick-swap memory device 13 allow the user to update and maintain the software and firmware within camera control unit 6.

Figure 2:
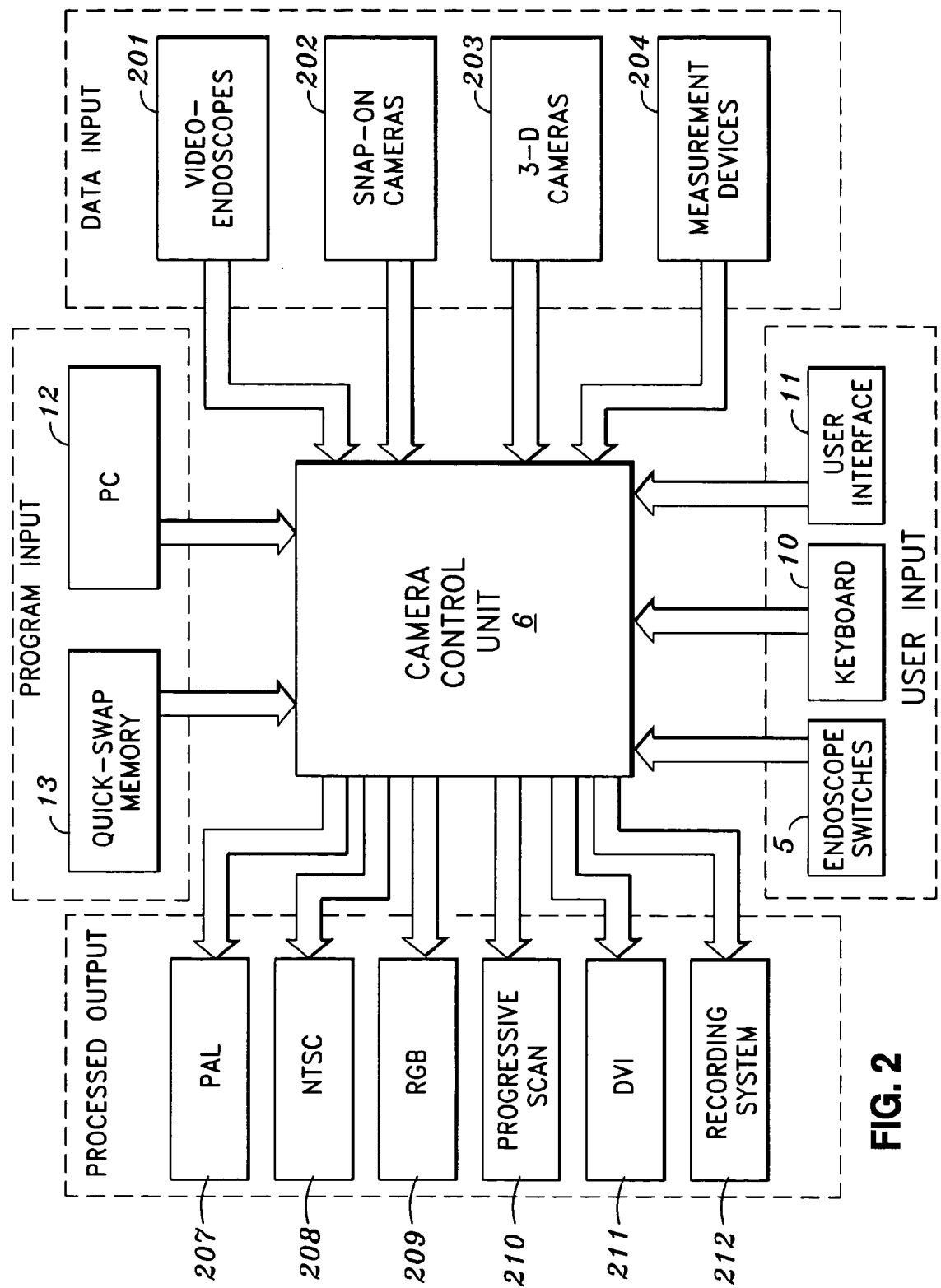
FIG. 2 is an Input/Output block diagram for a camera control unit in accordance with an exemplary embodiment of the present invention.

FIG. 2 shows other possible inputs and outputs of the present invention's camera control unit. Though typically used in conjunction with video endoscopes 201, camera control unit 6 is also able to control and process inputs from snap-on type cameras 202 used in conjunction with optical endoscopes (without an embedded image sensor), 3-D cameras 203, and other digital measurement devices 204. In addition, the camera control unit accepts program updates for the system's software and firmware through quick-swap flash memory device 13 or through a download from PC 12. Outputs of the camera control unit include analog output formats such as NTSC 207, PAL 208, RGB 209, and progressive scan 210. In addition, the camera control unit supports digital outputs for Digital Video Interface (DVI) 211 monitors as well as digital output for data recording to recording system 212, such as a hard disk drive.

Figure 3:
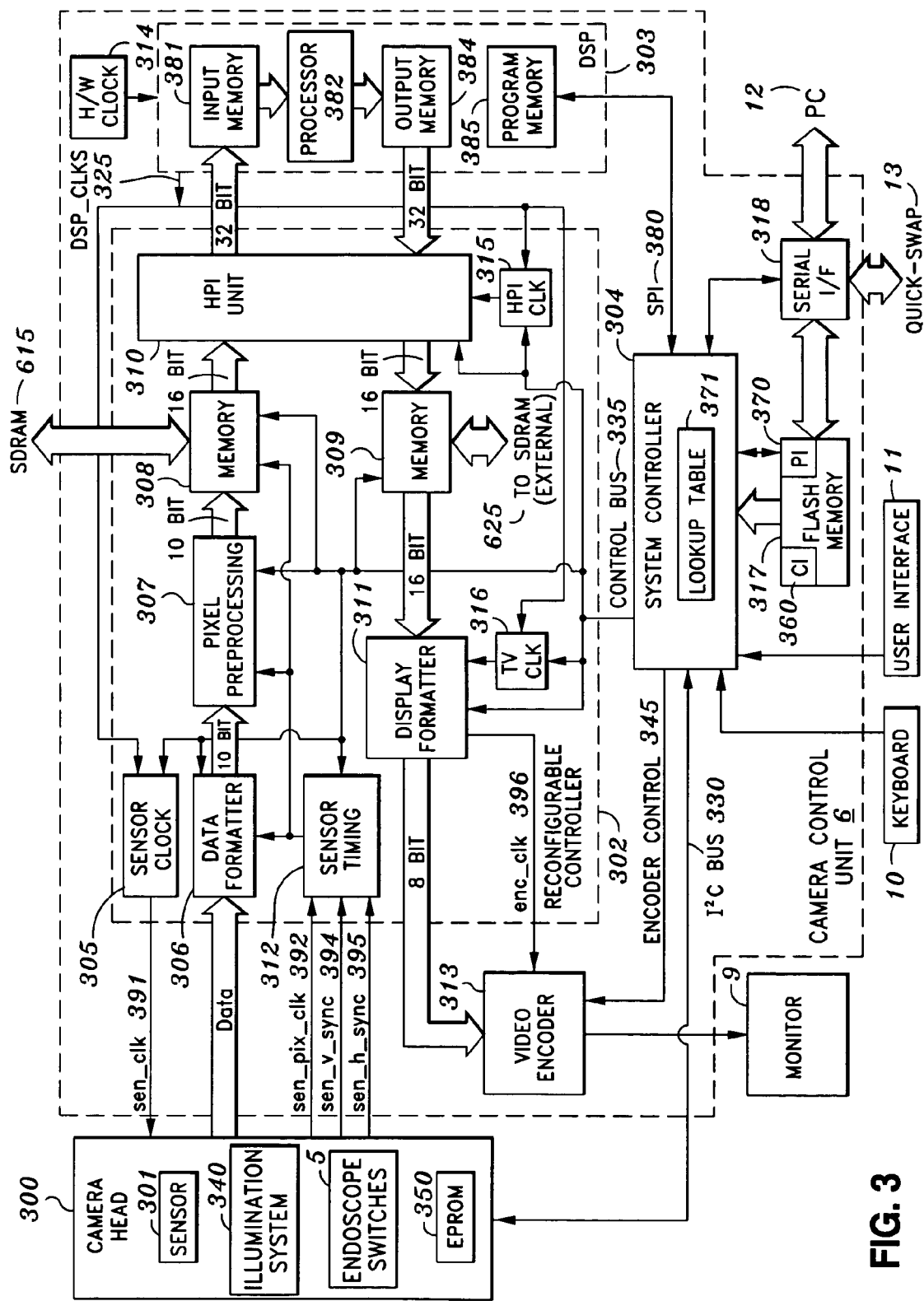
FIG. 3 is a block and data flow diagram for a camera control unit in accordance with an exemplary embodiment of the present invention.

FIG. 3 is a block diagram showing major components of camera control unit 6 (see FIG. 1), as well as the data path for the camera data captured by the sensor of an attached camera head, such as a video-endoscope. Major components of the camera control unit includes reconfigurable controller 302, digital signal processor ("DSP") 303, system controller 304, and video encoder 313. In a preferred embodiment, reconfigurable controller 302 is a FPGA, such as a Spartan 2-XILINX XC2S300E, manufactured by Xilinx of San Jose, Calif. While FPGA's are preferred, other types of programmable logic circuitry can be used, such as complex programmable logic devices (CPLD).

The camera data path begins at sensor 301 located in camera head 300. In a preferred embodiment, sensor 301 is a CMOS sensor located at the distal tip of a video-endoscope. Also included in camera head 300 is illumination system 340. Power, illumination, and camera control, such as automatic gain control and exposure time, are provided by system controller 304 to sensor 301 over inter-integrated circuit ("I²C") bus 330. The clock at which the sensor operates, sen_clk 391, is supplied by reconfigurable controller 302.

Each pixel of raw camera data generated by sensor 301 is transmitted to reconfigurable controller 302 at a gray-scale or color resolution of 8 or 10 bits, corresponding to 256 or 1024 gray-scale or color levels, respectively. Depending on the type of camera head, this raw camera data can be transmitted either in parallel, serial, or in a parallel/serial combination. In addition to raw camera data, and based on sen_clk signal 391 from reconfigurable controller 302, sensor 301 supplies a pixel clock (sen_pix_clk 392) as well as vertical and horizontal synchronization signals (sen_v_sync 394, sen_h_sync 395) to reconfigurable controller 302. The pixel clock determines the speed at which camera data pixels are clocked into reconfigurable controller 302. The vertical and horizontal synchronization signals indicate the start of each frame and line, respectively.

The raw camera data generated by sensor 301 is received by data formatter 306 in reconfigurable controller 302. Sensor clock generator 305 supplies sen_clk signal 391 to sensor 301, while sensor timing block 312 receives the pixel clock and synchronization signals from sensor 301. In addition, sensor timing block 312 generates image size control signals, such as start/end line and start end/pixel signals, based on the signals from sensor head 301. These signals may be used to specify a subset of the sensor area for which data is desired. For example, because of the configuration of the specific camera head, the sensor data might be windowed such that not all of the camera sensor data is used.

Together, the signals generated and received by sensor clock generator 305, data formatter 306, and sensor timing block 312 provide an electrical interface between an attached camera head sensor and camera control unit 6.

Data formatter 306 receives the raw camera data from sensor 301 at the rate of the pixel clock and formats the received pixels into a 10 bit parallel format. The data is then passed to pixel preprocessing block 307. At this point, pixel preprocessing may be performed, so as to compensate for sensor calibration and localized anomalies. Representative preprocessing is shown in FIG. 5.

Figure 5:
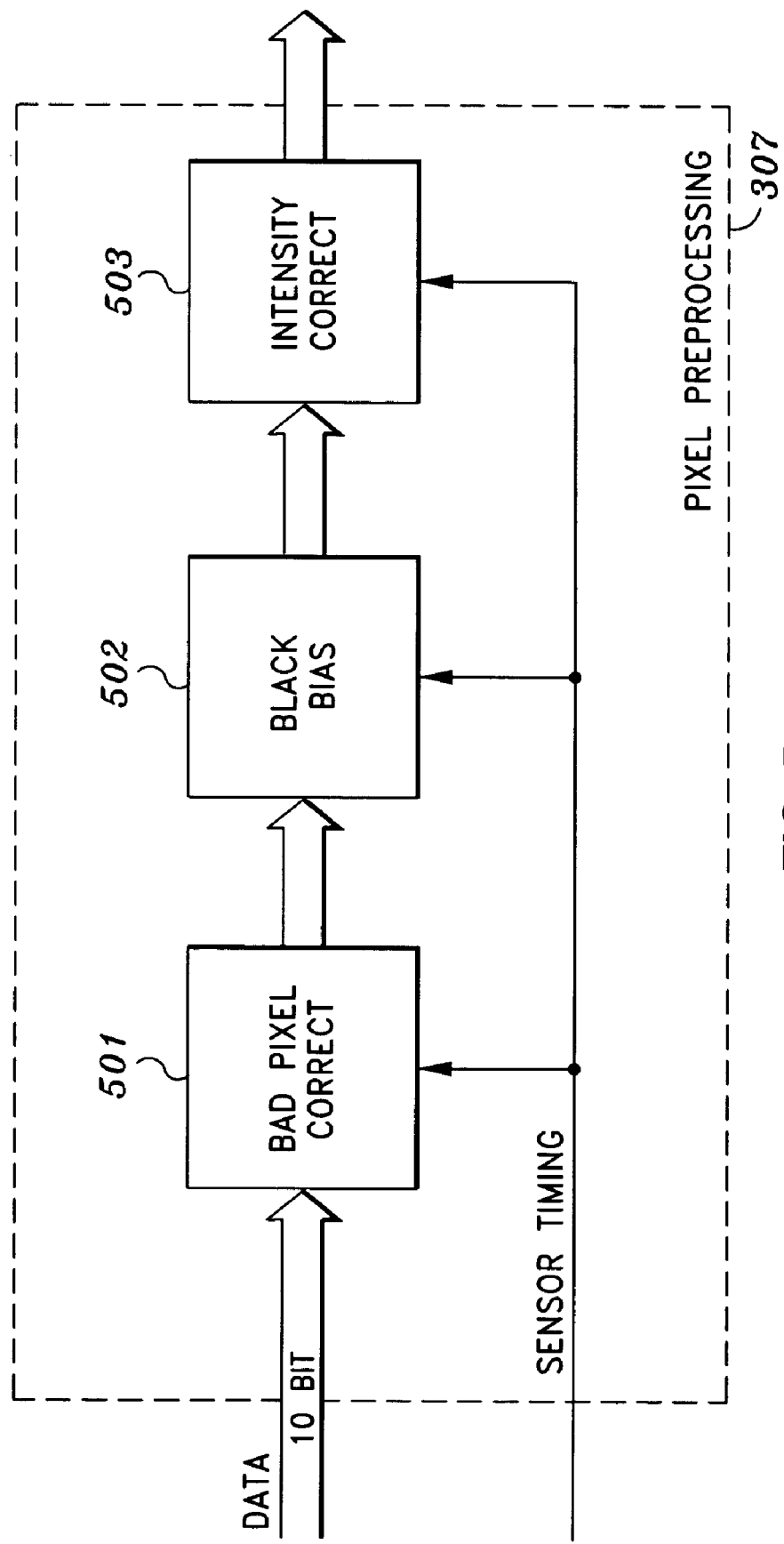
FIG. 5 is a block diagram illustrating pixel preprocessing in accordance with an exemplary embodiment of the present invention.

As shown in FIG. 5, pixel preprocessing can include preprocessing functions such as bad pixel correct 501, black bias 502, and intensity correct 503. The necessity of and types of pixel preprocessing functions that are implemented may be dependent on the type of sensor head used and the intended application.

As seen in FIG. 5, the clock rate at which the pixel preprocessing blocks operate is supplied by sensor timing block 312 (FIG. 3). In general, this rate depends on sen_pix_clk signal 392 supplied by sensor 301 (FIG. 3). In addition, sensor timing block 312 supplies a pixel counter and a line counter to bad pixel correct block 501 based on the dimensions of sensor 301. The pixel and line counters allow bad pixel correct block 501 to identify potentially faulty pixels within the frame generated by the attached sensor, and to correct them, such as through the use of median substitution.

Referring again to FIG. 3, after pixel preprocessing, the camera data (still in 10 bit format) is passed to memory 308. Typically, memory 308 is implemented as an asynchronous 16 bit first in, first out ("FIFO") register. The camera data is then passed from memory 308 to Host Processor Interface ("HPI") unit 310. HPI unit 310 packages the camera data into a 32 bit format and transfers it to internal input memory 381 in DSP 303. Data transfer is effected using direct memory access (DMA) protocol. In a preferred embodiment, DSP 303 is implemented as a TI TMS320C6414, manufactured by Texas Instruments of Dallas, Tex.

DSP 303 then performs an image processing operation on the received camera data as defined by program instructions stored in program memory 385. The program instructions are loaded into program memory 385 over serial port interface ("SPI") 380 by system controller 304. The processed camera data is stored in internal output memory 384.

After DSP 303 has processed the camera data, HPI unit 310 again uses DMA protocol to access the processed data from output memory 384. This 32 bit data is decoded to 16 bits and stored in memory 309. Like memory 308, memory 309 is typically implemented as an asynchronous 16 bit FIFO register. The processed camera data is then passed to display formatter 311 which adjusts the output timing and control signals for a selected output format. The output format can be selected with a switch on user interface 11 or by a selection on keyboard 10. In addition, display formatter 311 adds overlay text to the processed camera data.

The processed camera data is then passed to video encoder 313 along with an encoder clock signal (enc_clk 396) generated by display formatter 311 in accordance with the selected output format. After encoding, the video data is sent to monitor 9.

System controller 304 monitors and controls the flow of data along the above-described data path. System controller 304 controls the operation of sensor 301 and is responsible for loading software run by DSP 303 and for reconfiguring reconfigurable controller 302. In a preferred embodiment, system controller 304 is implemented as a Motorola 9HCS12 controller, manufactured by Motorola of Schaumburg, Ill.

The following sections discuss how system controller 304 interacts with the other components of camera control unit 6 to achieve the features of multi-head adaptability, multiple output capability, hardware acceleration, clock adjustability, user selectable configuration, and field programmable software and firmware.

[Multi-head Adaptability]

As mentioned above, one feature of the present invention lies in the ability of the camera control unit to reconfigure its functionality to adapt to different types of sensors and camera heads. In this way, one camera control unit may be used for multiple different heads.

Figure 4:
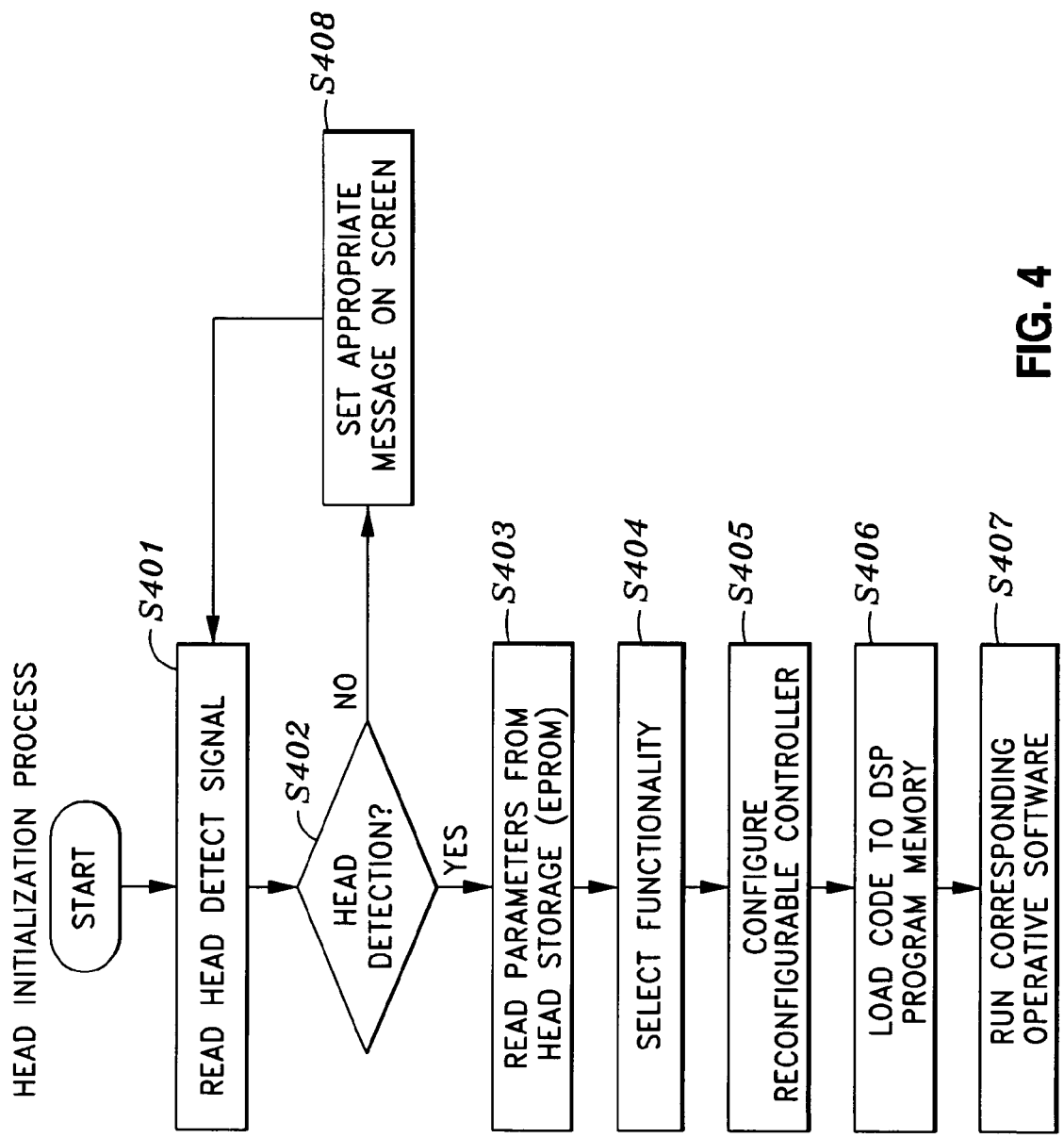
FIG. 4 is a process diagram of a head initialization process in accordance with an exemplary embodiment of the present invention.

FIG. 4 shows the head initialization process for the camera control unit performed by system controller 304 when a new camera head is attached. In step S401, system controller 304 polls for a head detect signal which might be supplied over I²C bus 330. If no signal is detected in step S402, step S408 displays a message on monitor 9 that indicates that no head is attached. Alternatively, a message could be displayed on a LCD screen located on user interface 11.

When a remote-head input device, such as flexible video endoscope 8, is attached to camera control unit 6, system controller 304 receives a head detect signal over I²C bus 330. Step S402 proceeds to step S403 where camera parameters stored in a readable camera parameter storage device, such as EPROM 350 located in camera head 300, are read by system controller 304 over I²C bus 330. The camera parameters may include such data fields as camera type, version, serial number, image size type, image format type, white balance reference matrix, color correct matrix, intensity correct lookup tables, and bad pixels index list.

In step S404, based on the camera parameters obtained in step S403, system controller 304 consults internal lookup cable 371 to determine what functionalities are available for the type of camera head attached. A camera parameter, such as camera type or serial number, is associated in lookup table 371 with one or more sets of configuration information and program instructions stored in a persistent re-writeable memory, such as a flash memory device or EEPROM. In FIG. 3, the persistent re-writeable memory is depicted as flash memory 317. The configuration information and program instructions define the functionality of the camera control unit.

If only one set of configuration information and program instructions is available for use with the attached camera head, that set is selected and the head initialization process proceeds to step S405. If multiple sets of configuration information and program instructions are available for the attached camera head, step S404 prompts the user to input a selection of the desired functionality. The user prompt may appear on monitor 9 or an LCD on user interface 11. The user selection may be accomplished through the use of tactile buttons on user interface 11, keyboard 10, or endoscope switches 5.

In step S405, based on the selection of functionality in step S404, system controller 304 obtains the selected set of configuration information 360 from flash memory 317 and configures reconfigurable controller 302 accordingly. In a preferred embodiment, configuration information 360 is a compiled VHDL program (where "VHDL" refers to VHSIC (very high speed integrated circuit) hardware description language). VHDL is a programming language used to configure programmable logic devices, such as FPGA's and CPLD's. In addition, other programming languages, such as Verilog, could also be used as configuration information 360, although it is preferred that the programming language is stored in flash memory 317 in compiled form. In a preferred embodiment, the selected configuration information is used to configure reconfigurable controller 302 by utilizing the FPGA programming pins. For example, the FPGA programming pins for the Spartan 2-XILINX XC2S300E are configuration data input pins D0-D7. On FIG. 3, the programming pins are generally represented by control bus 335.

In step S406, based on the selection of functionality in step S404, system controller 304 obtains the selected program instructions 370 from flash memory 317 and loads the program instructions into program memory 385 of DSP 303. Program instructions are program codes executable by DSP 303 and are loaded from flash memory 317 to DSP 303 by system controller 304 via serial port interface (SPI) bus 380.

Finally, in step S407 camera control unit 6 proceeds with normal operation by running the operative program instructions (i.e. software) in DSP 303, and the configuration information (i.e. firmware) loaded to configurable controller 302 as described above with reference to FIG. 3.

Referring back to step S405 and the configuration of reconfigurable controller 302, one portion of reconfigurable controller 302 that may become reconfigured in response to a new camera head is the control circuitry for the electrical interface. As discussed above, the signals generated and received by sensor clock generator 305, data formatter 306, and sensor timing block 312 provide the electrical interface between an attached camera head and camera control unit 6. Altering how the signals of the electrical interface are generated and manipulated is one aspect of reconfiguring reconfigurable controller 302 to adapt to a different head.

Referring again to FIG. 3, one signal that is set based on a different camera head attached is the sensor clock signal generated by sensor clock generator 305. Sensor clock generator 305 receives an input DSP clock signal (DSP_CLK 325) from DSP 303. Sensor clock generator 305 may be arranged as a divider or a controllable phase-locked-loop circuit which system controller 304 can configure using control bus 335. In a preferred embodiment, the input DSP clock signal is 96 MHz which can be used by the sensor clock generator 305 to generate clock signals of 48, 24, 16, 12, 8 or 3 MHz. For example, a camera head with a sensor size of 352×288 may only require a sensor clock of 12 MHz, while a larger 1024×790 sensor may require a sensor clock of 48 MHz. In addition to using sensor clock generator 305 to generate the sensor clock signal from a DSP clock signal, DSP 303 may also be used to generate the sensor clock signal directly, or the generation of the sensor clock signal may be split between DSP 303 and sensor clock generator 305.

Sensor timing block 312 is reconfigured based on the type of camera head so as to generate signals tailored to the connected camera head from the clock and synchronization signals received from the camera head. Generally, sensor timing block 312 passes the pixel clock and synchronization signals generated by the sensor to data formatter 306, pixel preprocessing block 307, and memory 308. In addition, sensor timing block 312 generates line counters and pixel counters for bad pixel correct 501 (of FIG. 5) in pixel preprocessing block 307, and the generation of these signals depends on the type of camera head. These line and pixel counters may be dependent on the sensor size of the camera head, and thus can be configured into sensor timing block 312 by controller 304 through control bus 335.

Additionally, sensor timing block 312 can be reconfigured to generate image size control signals, such as start/end line and start/end pixel control signals. These signals mark the start and end of a valid data area or window of the image sensor. In effect, these signals allow the camera control unit to discard camera data from defined areas of the image sensor and only process camera data from a desired area. For example, an image sensor for a snap-on camera may have a rectangular shape. However, since the sensor of a snap-on camera "looks through" the circular eyepiece of an optical endoscope, data around the edges may be unneeded if the sensor viewing area is larger than the eyepiece viewing area. Through the use of the start/end line and start/end pixel control signals, camera data from the edges can be discarded, thus improving processing speed. Similarly, the start/end line and start/end pixel control signals can be used to define an area for digital zoom.

A further aspect of the electrical interface that may become reconfigured is that of data formatter 306. As mentioned above, data formatter 306 typically receives 8 or 10 bit raw camera data from sensor 301 and arranges it into a 10 bit parallel format. However, since the logic circuitry of data formatter 306 can be reconfigured by system controller 304 using control bus 335, other data formats may be created. For instance, larger bit formats may be beneficial for higher resolution sensors. In addition, it may be necessary to reconfigure data formatter 306 to accept data streams of varying formats, such as parallel or serial data.

Reconfiguration is not limited to the electrical interface. Other aspects of reconfigurable controller 302 may also be reconfigured. For example, in pixel preprocessing block 307, different processing functions may be beneficial for different camera heads. As with the electrical interface control circuitry, system controller 304 may reconfigure pixel preprocessing block 307 in response to a new camera head attachment. As before, reconfiguration is achieved through the control bus 335. System controller 304 associates the received camera parameters with configuration information stored in flash memory 317 and reconfigures pixel preprocessing block 307 with the preprocessing functions used for the attached camera head. In addition, for certain preprocessing functions, rather than storing the necessary matrices and lookup tables in the flash memory, specific fields of the camera parameter data can be loaded into pixel preprocessing block 307, such as white balance reference matrix, color correct matrix, intensity correct lookup tables, and bad pixels index list.

Another block in reconfigurable controller 302 that may be reconfigured for a new camera head is memory 308. While for most sensor sizes, memory 308 is implemented as an asynchronous 16 bit FIFO, larger amounts of memory may be needed for larger sensors. In addition, for some programs stored in program memory 385 of DSP 303, the 16 bit FIFO registers may not have enough capacity. In this case, system controller 304 can reconfigure memory 308 to act as a controller for writing to a memory external to the reconfigurable controller, such as an SDRAM, indicated generally at 615 in FIG. 3 and discussed more fully below.

Figure 6A:
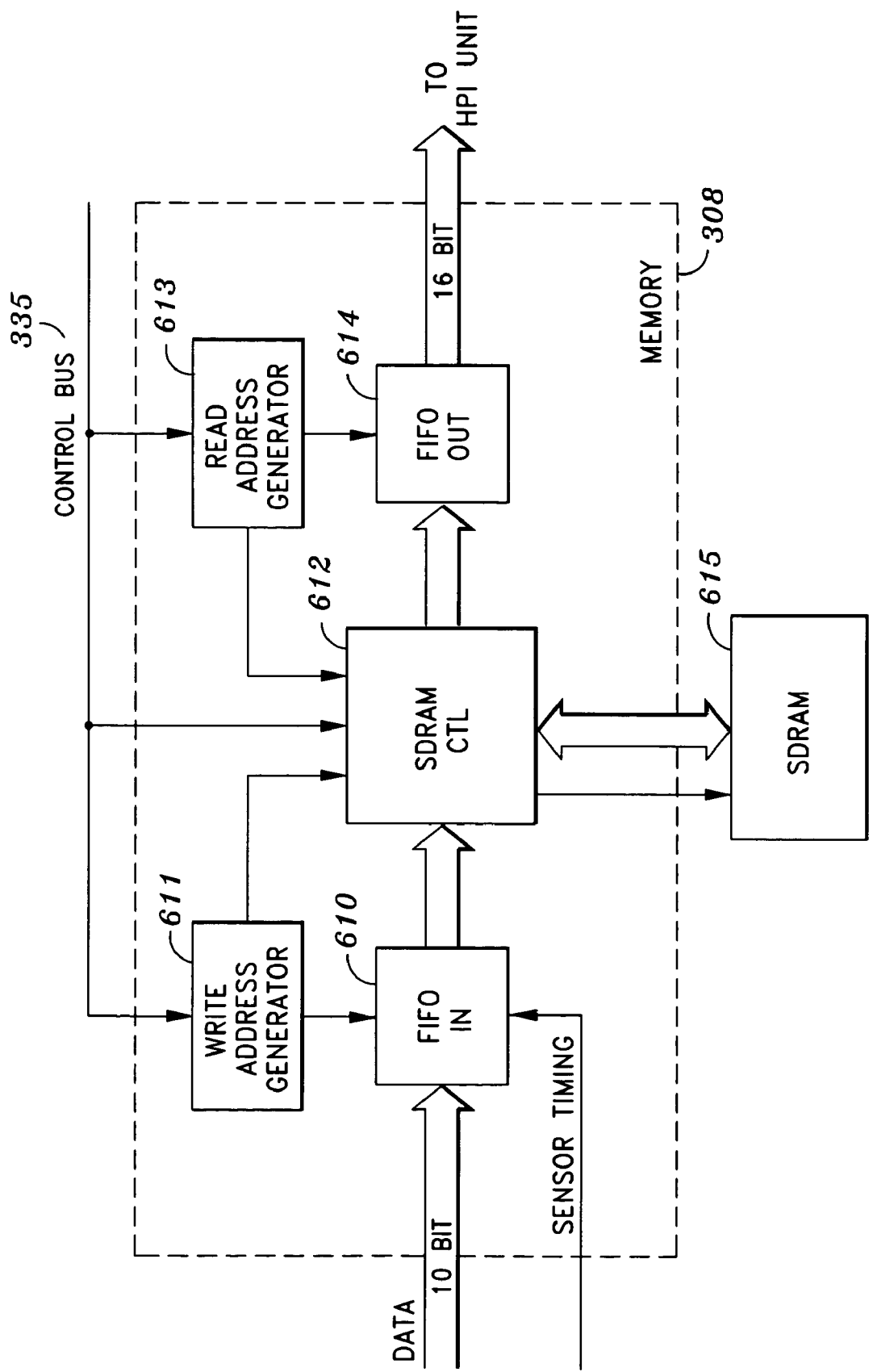
FIG. 6A is a block diagram illustrating input external memory control in accordance with an exemplary embodiment of the present invention.

FIG. 6A depicts this additional configuration. As show in FIG. 6A, input FIFO 610 receives a 10 bit data signal from pixel preprocessing block 307. This data is clocked in based on the sensor timing signal, which is typically sen_pix_clk 392 generated by sensor 301. System controller 304 uses control bus 335 to configure write address generator 611 to generate write addresses used by SDRAM controller 612. The SDRAM controller takes the data from the input FIFO as well as the write address generator and writes the camera data to external SDRAM 615.

For retrieving the data from SDRAM 615, system controller 304 configures read address generator 613 to generate read addresses used by SDRAM controller 612. Using this address, SDRAM 612 retrieves the addressed data from SDRAM 615 and passes the camera data to output FIFO 614. The data is reformatted to 16 bits by padding before passing to HPI unit 310.

Figure 6B:
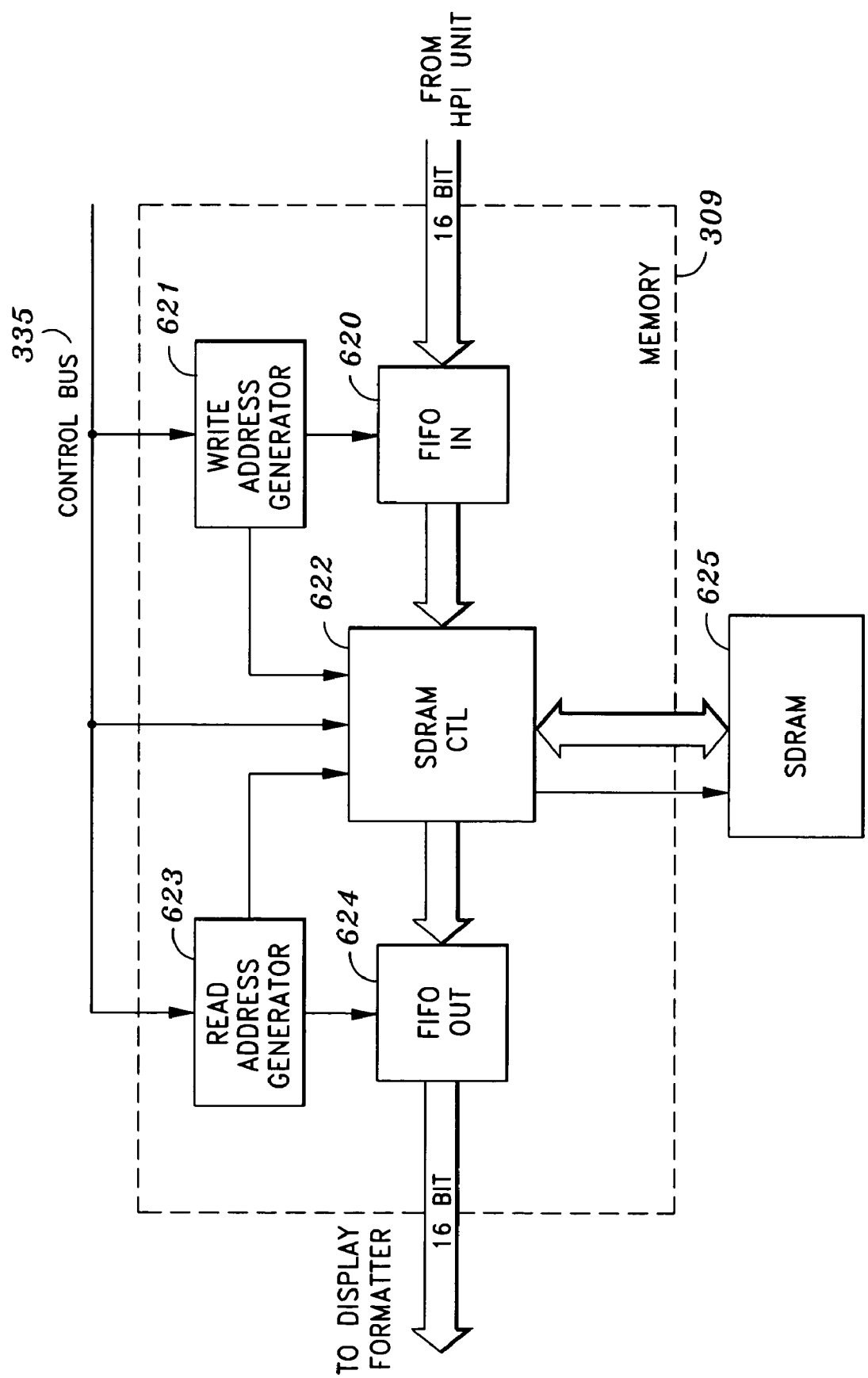
FIG. 6B is a block diagram illustrating output external memory control in accordance with an exemplary embodiment of the present invention.

FIG. 6B depicts a similar arrangement for passing already processed image data from HPI unit 310 to display formatter 311. More specifically, input FIFO 620 receives a 16 bit data signal from HPI unit 310. System controller 304 uses control bus 335 to configure write address generator 621 to generate write addresses used by SDRAM controller 622. The SDRAM controller takes the data from input FIFO 620 as well as write address generator 621 and writes the camera data to external SDRAM 625. For retrieving the data from SDRAM 625, system controller 304 configures read address generator 623 to generate read addresses used by SDRAM controller 622. Using this address, SDRAM 622 retrieves the addressed data from SDRAM 625 and passes the camera data to output FIFO 624. The data is then passed to display formatter 311.

Referring again to FIG. 3, and as previously mentioned, DSP 303 can be programmed by loading program instructions 370 from flash memory 317 into DSP 303 program memory 385 using SPI bus 380. These program instructions are loaded with various objectives in mind, such as programs that effect particularized image processing based on the type of camera head, and/or programs responsive to preferences selected by a user. The latter will be discussed in the section entitled "User Selectable Software" below. In the former, program instructions that are loaded are associated with the camera head detected by system controller 304. Examples of camera head-dependent program instructions performed by DSP 303 include intensity correction, edge enhancement, and color smoothing.

While all the reconfigurations mentioned above are performed in response to detecting a new camera and reading its camera parameters, camera identification can be obtained without necessarily reading it from a readable camera parameter storage device. For example, a new head can be identified through a calibration process. In addition, camera features such as sensor size may be inferred from synchronization signals.

[Multiple Output Capability]

The multiple output capability of the present invention allows the user to select from a plurality of video formats for the display of processed camera data. For example, the user could choose among NTSC, PAL, and RGB formats depending on the type of display being used. Referring to FIG. 2, the user may select the video output format by using controls on user interface 11 of camera control unit 6 or by a selection with keyboard 10. In addition, selection could be made by a selection via software on PC 12 attached to camera control unit 6.

Referring again to FIG. 3, once the user makes a video output selection, system controller 304 notifies the selection to video encoder 313 via encoder control line 345 and configures reconfigurable controller 302. For example, if the user selects NTSC output, system controller 304 sends a signal prompting video encoder 313 to encode the sensor data signal at 525 lines/frame and configures TV clock generator 316 to generate a 60 Hz clock signal. On the other hand, if the user selects PAL output, the signals from system controller 304 prompts encoding at 625 lines/frame and configures TV clock generator 316 to generate a 50 Hz clock signal.

Figure 8:
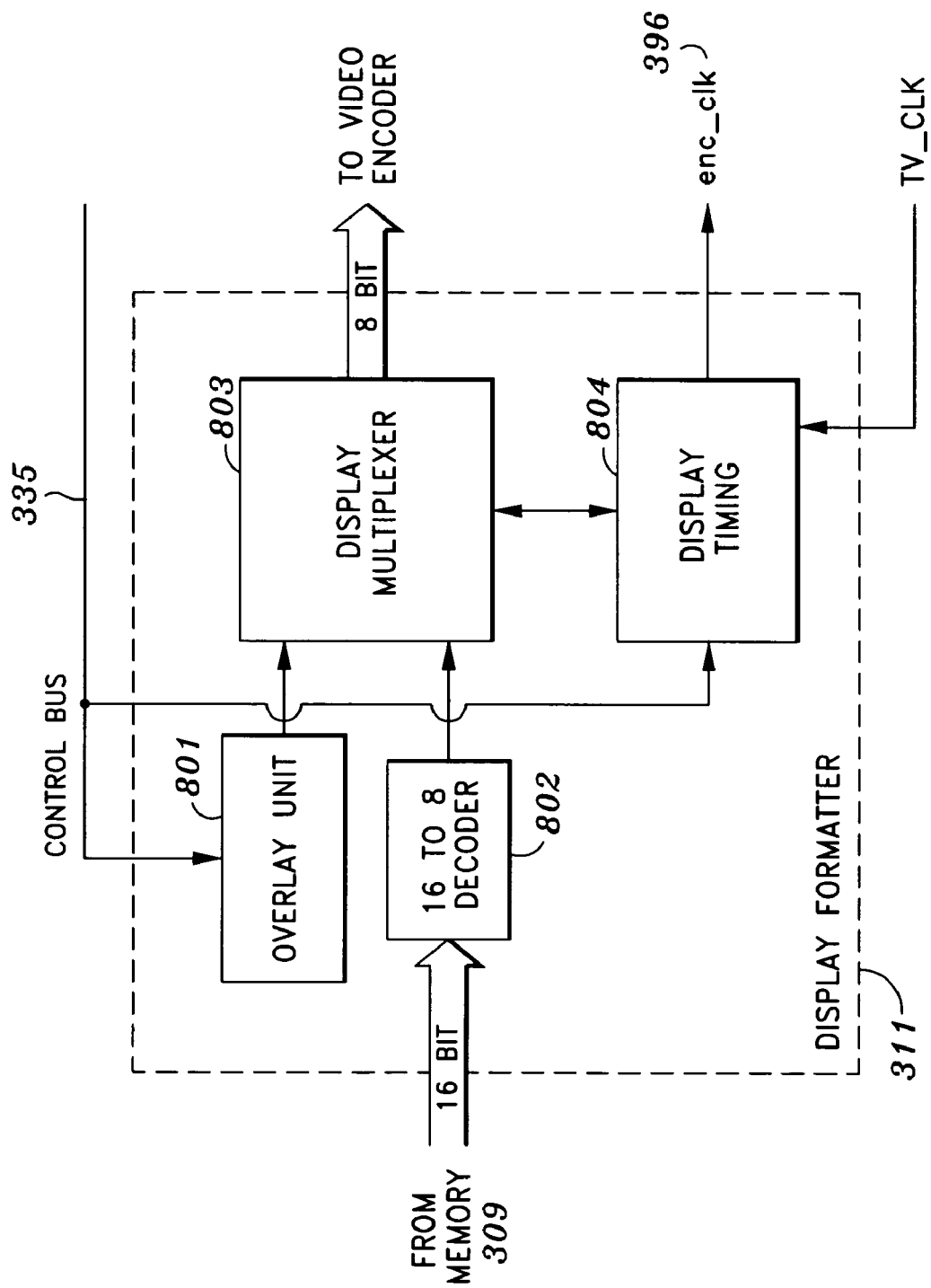
FIG. 8 is a block diagram for a display formatter in accordance with an exemplary embodiment of the present invention.

With respect to configuration of reconfigurable controller 302, system controller 304 sends a signal to display formatter 311 via control bus 335. Referring to FIG. 8, this signal reconfigures display timing block 804 to generate start/end pixel and start/end line control signals which identify valid data based upon the desired display dimensions. Display timing block 804 also generates frame number data for cursor activation. Thus, system controller 304 reconfigures the output timing signals generated by display timing block 804 in response to the user's selection of video format. Enc_clk 396 is sent to video encoder 313 and may also be used to synchronize the display of text data with the processed sensor data as described below.

Display formatter 311 receives the processed sensor data signal from memory 309 and converts the data format from 16 bits to 8 bits using decoder 802. The converted data is then sent to display multiplexer 803. Overlay unit 801 receives a signal containing overlay text data from system controller 304 via control bus 335 and receives a signal containing timing data from display timing block 804. Overlay unit 801 generates a contour for the overlay text data and cursor and sends the properly timed text data signal to display multiplexer 803. Display multiplexer 803 combines the processed sensor data signal and the text data signal, sending the combined signal to video encoder 313.

In an alternate arrangement, text data need not be combined with sensor data. For example, text may be displayed on its own screen, separate from the sensor data. This arrangement obviates the use of the overlay unit and the display multiplexer.

Figure 9:
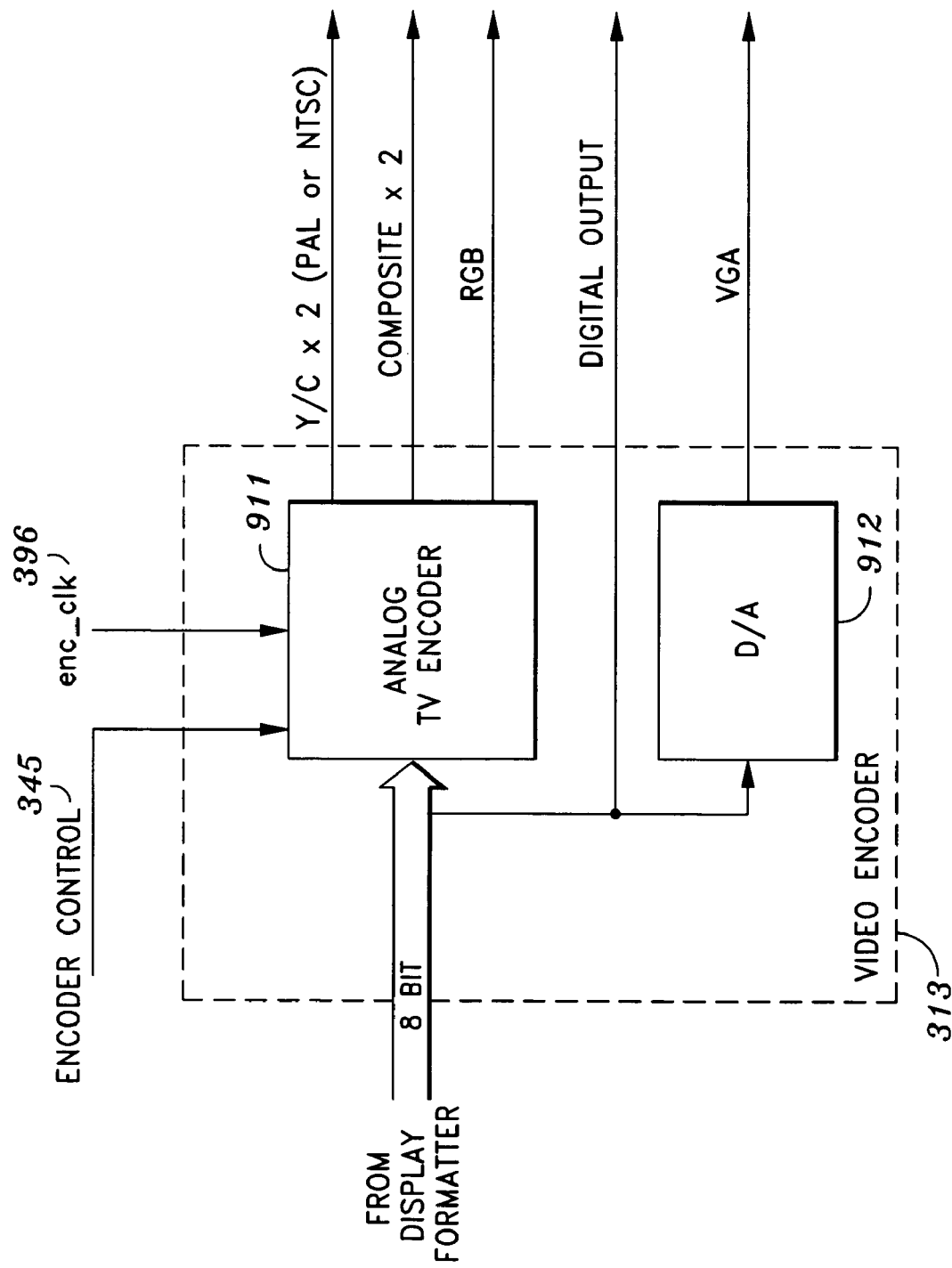
FIG. 9 is a block diagram illustrating a video encoder in accordance with an exemplary embodiment of the present invention.

Referring again to FIG. 3, video encoder 313 receives sensor data and enc_clk 396 from display formatter 311 and encoder control signal 345 from system controller 304. The configuration of video encoder 313 is shown in FIG. 9. Referring to FIG. 9, analog TV encoder 911 encodes the processed sensor data into the video format prompted by encoder control signal 345 received from system controller 304. Thus, analog TV encoder 911 reconfigures the display format in response to the user's selection of video format such as PAL or NTSC, composite or RGB. In addition, digital to analog (D/A) converter 912 may also be used to convert the sensor data to a VGA output. Video encoder 313 may also include a pass-though for the sensor data allowing the output of digital sensor data for display on a DVI monitor or for recording on a hard disk drive. Therefore, video encoder 313 may have multiple outputs including the user-selected video format.

[Hardware Acceleration]

Referring again to FIG. 3, the FPGA of reconfigurable controller 302 is programmed to handle input and output processing on behalf of DSP 303. Since it is the FPGA that is responsible for input and output processing, DSP 303 is freed from these tasks and is able to devote its processing power to the task of image processing. As discussed above with reference to the feature of multi-head adaptability, reconfigurable controller 302 is configurable to accommodate sensors with largely varying time bases, input data format, and pixel preprocessing requirements. In addition, sensor timing block 312 is able to adjust the input timing so as to implement a non-optical digital zoom function. Furthermore, reconfigurable controller 302 is configurable to generate different output formats and timing. Thus, the reconfigurable controller acts as the interface between the sensor and the DSP as well as between the DSP and the output. In this way, the camera control unit can achieve enhanced throughput and less delay.

More specifically, one way in which reconfigurable controller 302 increases throughput is by acting as the interface between sensor 301 and DSP 303. As described above, reconfigurable controller 302 supplies timing to the sensor, formats the incoming data, performs any necessary pixel preprocessing on the data, and stores the incoming data in memory for use by the DSP. Conversely, reconfigurable controller 302 accesses data already processed by the DSP from a memory, formats the data for display, and delivers it to a video encoder.

Figure 7:
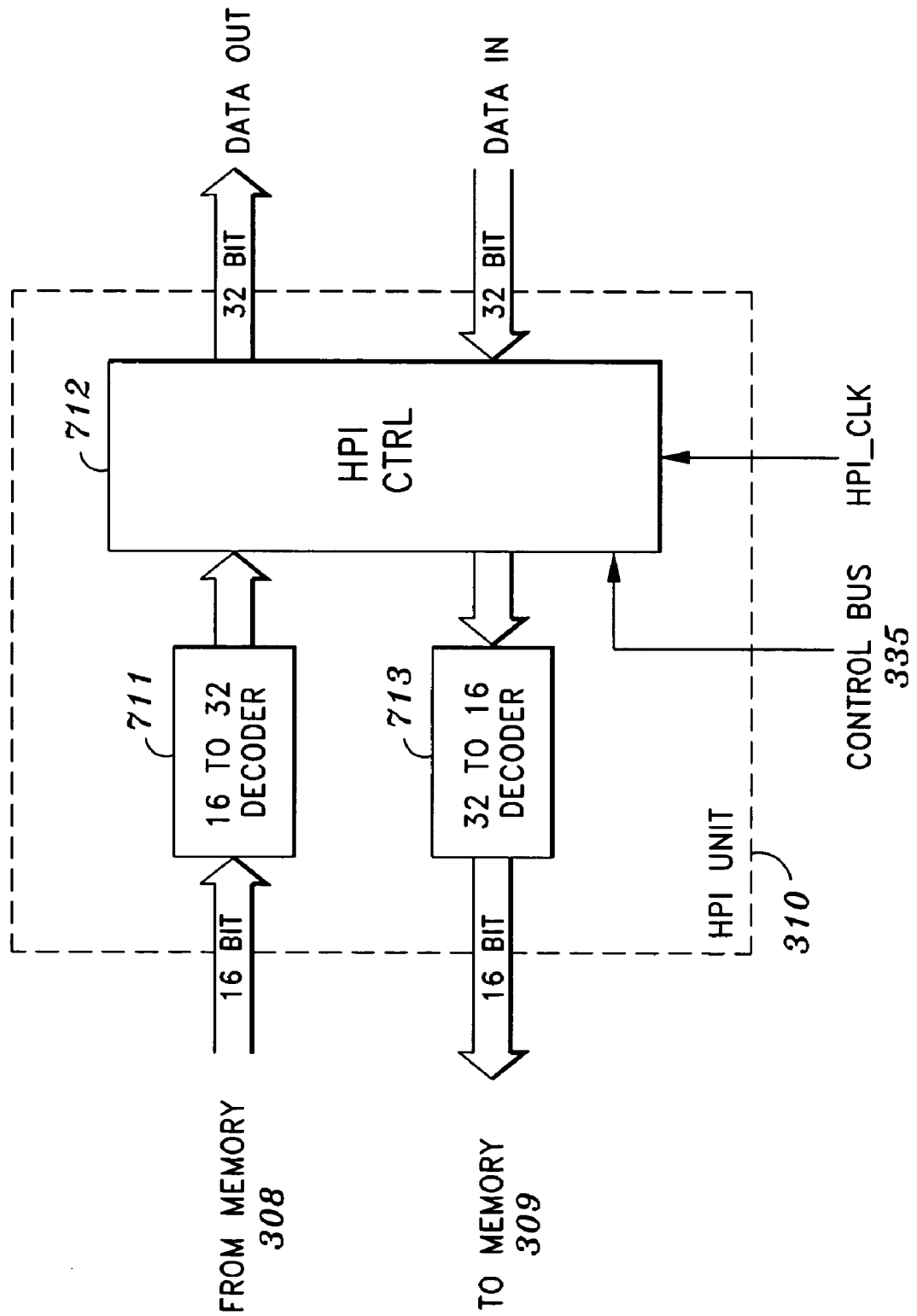
FIG. 7 is a block diagram for a Host Processor Interface (HPI) unit in accordance with an exemplary embodiment of the present invention.

FIG. 7 illustrates the interface with the DSP in more detail. Camera data is passed from memory 308 (of FIG. 3) to HPI unit 310. Within HPI unit 310, decoder 711 packages the 16 bit data from memory 308 into a 32 bit data format. Then HPI controller 712 clocks the 32 bit data to input memory 381 of DSP 303 (both of FIG. 3) at the HPI clock rate (typically 40 MHz). The HPI controller uses direct memory access (DMA) protocol to send the data to input memory 381 of DSP 303. In this way, DSP resources are not wasted on data transfer.

Likewise, when DSP 303 has finished processing a certain number of camera data lines (preferably two lines of camera data), HPI controller 712 utilizes DMA to clock the processed camera data back into reconfigurable controller 302 from output memory 384. Decoder 713 then converts the 32 bit data to a 16 bit format and sends the processed data to memory 309 and then on to display formatter 311 (of FIG. 3). In this way, reconfigurable controller 302 also acts as a DSP to output interface.

[Clock Adjustability]

Another feature of the present invention lies in the use of a hardware clock signal from which other clock signals can be generated at clock frequencies adjustable by software. Referring back to FIG. 3, hardware clock 314 supplies a clock signal to DSP 303. From this clock signal, DSP 303 generates two DSP clock signals, DSP_CLKS 325. In a preferred embodiment, hardware clock 314 generates a 48 MHz signal, while DSP 303 generates clock signals of 144 MHz and 96 MHz. These two clock signals are supplied to reconfigurable controller 302. Although in this embodiment it is the DSP that generates DSP_CLKS 325, it is possible that these clocks are generated by other hardware in the camera control unit.

Reconfigurable controller 302 utilizes the DSP clock signals to generate clock signals for the sensor, display formatter, video encoder, and HPI unit. As discussed above with reference to sensor clock generator 305, the clock generators in reconfigurable controller 302 are typically implemented as dividers or controllable phase-locked-loop circuits. Sensor clock generator 305, HPI clock generator 315, TV clock generator 316, and the encoder clock are each configurable by system controller 304. By providing separate clock generators for each phase of the data flow, the camera control unit is able to alter input and output timing independently.

Altering input and output timing independently is beneficial since it is typically necessary to conform the output timing of a video system to the timing requirements of the output device (e.g. NTSC or PAL). However, the requirements for input timing are generally much more variable. Factors such as amount of motion in the image, intensity of light available, and type and size of sensor used can affect what input timing is optimal. By providing a software controllable clock for input timing, fine adjustments can be made. For example fine adjustments could be made to the sensor exposure timing instead of using gain amplifiers to improve the signal. This is desirable, as gain amplifiers generally introduce noise. Furthermore, since the output timing signal is independent of the input timing signal, fine adjustments to input timing will not produce timing anomalies in the output video signal.

[User Selectable Configuration]

According to another feature of the present invention, a user is able to select, such as by selection from a menu of plural options, the program instructions (i.e. software) and configuration information (i.e. firmware) used by the camera control unit. Using an input device, such as keyboard 10 or user interface 11 (both of FIG. 1), a user can instruct system controller 304 to load a specific set of configuration information and program instructions to be carried out by reconfigurable controller 302 and DSP 303. In addition, selection may be accomplished using endoscope switches 5 on the camera head itself.

According to one preferred embodiment of this aspect of the invention, after system controller 304 has detected a new camera head, rather than reconfiguring the reconfigurable controller and loading program instructions into the DSP with predetermined firmware and software, the user may be prompted to select from among two or more sets of configuration information and program instructions, each directed to use for different medical applications or conditions. In some instances, an attached camera head may only have one set of configuration information and program instructions. In the case that there are multiple sets, a user may be given the option of selecting, for example, a profile for standard configuration information and program instructions settings, or a profile that performs better in low light conditions. Once the user selects the program instructions to be performed, system controller 304 accesses flash memory 317 to obtain the selected program instructions and then loads them into DSP 303 for execution as described with reference to the feature of multi-head adaptability. In addition, system controller 304 reconfigures reconfigurable controller 302 with the selected configuration information. As with the changes executed when a new head is detected, the selection of different configuration information and program instructions is not limited to changing simple numerical data points, such as gain factors and filter characteristics. Instead, a user selection of configuration information allows for significant hardware changes used for different applications, such as shifting the time base and digital zoom.

[Field Programmable Software and Firmware]

Another feature of the present invention is the ability to upgrade both the software (program instructions) and firmware (as configured by the configuration information) available to the camera control unit in the field. "In the field" refers to the time after which the camera control unit has been delivered to an end user, such as a hospital. Program instructions 370 and configuration information 360 utilized by camera control unit 6 are stored in flash memory 317. One way in which flash memory 317 can be updated is through a PC download. Referring again to FIG. 3, camera control unit 6 includes a serial port interface 318 which is connectable to PC 12. System controller 304 controls the transfer of program instructions and configuration information from the PC through the interface to flash memory 317. In addition, flash memory 317 can also be updated through the use of quick-swap flash memory 13. Like a PC download, the quick-swap device is connected to the serial port interface of the camera control unit, and the download is powered and controlled by system controller 304. Either of these upgrade possibilities can be performed by suitably trained personnel without the need to return the camera control unit back to the manufacturer or service center.

In combination with the feature of a reconfigurable controller and DSP, by allowing both the software and the firmware to be upgraded in the field, the present invention's camera control unit is able to adapt to new camera heads, pixel preprocessing algorithms, and image processing software without a change of hardware.

The feature of field-programmable software and firmware also contemplates the redistribution of functionality from their current assignments between reconfigurable controller 302 and DSP 303. As discussed above, input and output processing together with some preprocessing is handled by reconfigurable controller 302, while image processing is handled by DSP 303. Upgrading the software and firmware in the field may include shifting some of the image processing operations typically handled by DSP 303 to reconfigurable controller 302. Likewise, input and output processing and/or preprocessing operations could be shifted so as to be handled by DSP 303.

The invention has been described above with respect to particular illustrative embodiments. It is understood that the invention is not limited to the above-described embodiments and that various changes and modifications may be made by those skilled in the relevant art without departing from the spirit and scope of the invention. Thus, the present embodiments of the invention should be considered in all respects as illustrative and not restrictive, the scope of the invention to be determined by any claims supported by this specification, accompanying drawings, and the claims' equivalents rather than the foregoing description.

What is claimed is:

1. A camera control unit for controlling operation of a sensor head and for processing raw camera data received from the sensor head, the camera control unit comprising:
   an electrically-connected assembly comprising:
      an electrical interface detachably connectable to a sensor head, the sensor head comprising an image sensor disposed in a housing;
      a reconfigurable controller for timing and control of the sensor head over the electrical interface, wherein the electrical interface receives the raw camera data from the image sensor, wherein the reconfigurable controller comprises: a sensor clock generator for generating a sensor clock signal used by the sensor; a data formatter for converting the received camera data into a standard format; and a sensor timing block for supplying an input pixel clock and image size control signals to the data formatter, said image size control signals are associated with the raw camera data received from the sensor head;
   a system controller capable of:
      detecting a connection of a sensor head,
      recognizing identification information about the sensor head on the connection,
      comparing the identification information with stored sensor-head information for a plurality of sensor-head types, and
      matching the identification information with a matching, stored sensor-head information;
   wherein the system controller being able to use the matching, stored sensor-head information to reconfigure the reconfigurable controller for timing and control of the image sensor;
   wherein the assembly is disposed outside and apart from the housing of the sensor head; and
   wherein pixel preprocessing operations include bad pixel correct, black bias, and intensity correct; and
   wherein the sensing timing block supplies a pixel counter and a line counter to the bad pixel correct block based on the dimensions of the sensor to identify potentially faulty pixels generated by the sensor and to correct them through the use of median substitution.

2. The camera control unit of claim 1 wherein the identification information includes any of camera type, camera version, camera serial number, or camera image size type.

3. The camera control unit of claim 1, wherein the reconfigurable controller is a field-programmable gate array.

4. The camera control unit of claim 1, wherein the standard format is a 10 bit parallel format.

5. The camera control unit of claim 1, wherein the image size control signals include start/end pixel and start/end line pixel control signals.

6. The camera control unit of claim 5 wherein the system controller reconfigures the start/end pixel and start/end line pixel control signals to effect a digital zoom.

7. The camera control unit of claim 1 wherein the sensor clock generator is a controllable divider.

8. The camera control unit of claim 1, further comprising:
pixel preprocessing circuitry contained in the reconfigurable controller, wherein the pixel preprocessing circuitry performs preprocessing operations on the received camera data.

9. The camera control unit of claim 8 wherein the pixel preprocessing circuitry is reconfigured by the system controller based on the identification information to perform different preprocessing operations.

10. The camera control unit of claim 1, further comprising a digital signal processor for performing an image processing operation on the received camera data; and
wherein the system controller loads the image processing operation into the digital signal processor based on the identification information.

11. The camera control unit of claim 10, wherein the system controller matches the identification information to a lookup table entry associated with configuration information and program instructions stored in a memory.

12. The camera control unit of claim 11, wherein the system controller reconfigures the reconfigurable controller with the associated configuration information, and wherein the system controller loads the image processing operation performed by the digital signal processor by loading the associated program instructions in the digital signal processor.

13. The camera control unit of claim 1, further comprising an endoscope, the sensor head being disposed on or in the endoscope.

* * * * *